United States Patent
Cox et al.

(10) Patent No.: US 9,267,844 B2
(45) Date of Patent: Feb. 23, 2016

(54) METHOD AND APPARATUS FOR CORRECTING BIAS ERROR IN RING-DOWN SPECTROSCOPY

(75) Inventors: James Allen Cox, New Brighton, MN (US); Teresa M. Marta, White Bear Lake, MN (US)

(73) Assignee: HONEYWELL INTERNATIONAL INC., Morristown, NJ (US)

(*) Notice: Subject to any disclaimer, the term of this patent is extended or adjusted under 35 U.S.C. 154(b) by 668 days.

(21) Appl. No.: 13/478,156

(22) Filed: May 23, 2012

(65) Prior Publication Data
US 2013/0314715 A1    Nov. 28, 2013

(51) Int. Cl.
| | |
|---|---|
| G01N 21/00 | (2006.01) |
| G01B 9/02 | (2006.01) |
| G01J 3/28 | (2006.01) |
| G01J 3/30 | (2006.01) |
| G02B 5/08 | (2006.01) |
| H01S 3/00 | (2006.01) |
| H01S 3/11 | (2006.01) |
| H01S 3/10 | (2006.01) |
| G01J 3/42 | (2006.01) |
| G01N 21/3504 | (2014.01) |
| G01N 21/31 | (2006.01) |

(52) U.S. Cl.
CPC . *G01J 3/42* (2013.01); *G01N 21/31* (2013.01); *G01N 21/3504* (2013.01)

(58) Field of Classification Search
CPC ... G01N 21/31; G01N 21/3504; G01N 21/64; G01N 21/534; G01N 21/1702; G01J 3/42; G01J 3/10
USPC .............. 356/454, 326, 436, 317, 437, 480; 359/341.4, 857; 372/10, 20
See application file for complete search history.

(56) References Cited

U.S. PATENT DOCUMENTS

| | | | |
|---|---|---|---|
| 2005/0117620 A1* | 6/2005 | Thro | H01S 3/2383 372/70 |
| 2007/0064748 A1* | 3/2007 | Mirov et al. | 372/20 |
| 2009/0185175 A1* | 7/2009 | Cole et al. | 356/213 |
| 2010/0188661 A1 | 7/2010 | Cole | |
| 2011/0199611 A1 | 8/2011 | Cole et al. | |
| 2011/0317164 A1 | 12/2011 | Cole et al. | |

* cited by examiner

*Primary Examiner* — Tarifur Chowdhury
*Assistant Examiner* — Sunghee Y Gray
(74) *Attorney, Agent, or Firm* — Husch Blackwell LLP

(57) ABSTRACT

An apparatus is provided. The apparatus includes a laser source and a ring-down optical resonator that performs cavity ring-down spectroscopy, the optical resonator receives coherent optical energy from the laser, wherein an extinction rate of optical resonance within the optical resonator is at least 100 times longer than an extinction rate of optical energy emitted from the laser source first following deactivation of the laser source.

10 Claims, 4 Drawing Sheets

METHOD AND APPARATUS FOR CORRECTING BIAS ERROR IN RING-DOWN SPECTROSCOPY

FIELD

The field of the invention relates to cavity ring-down spectroscopy and more particularly to methods of correcting measurement errors.

BACKGROUND

Spectroscopy is generally known. Spectroscopy relies upon that fact that the atoms and molecules of most materials will absorb radiation of a specific wavelength. In spectroscopy, a sample is bombarded with a radiant signal from a radiant source that is swept through a predetermined frequency range. A detector measures the amount of radiation absorbed at each frequency by the sample as the source is swept through the frequency range in order to determine a composition of the sample.

Devices that use cavity ring-down spectroscopy are also generally known. Such devices provide a highly reliable and accurate method of detecting both the presence and levels of a variety of different gaseous materials.

In general, cavity ring-down spectroscopy is based upon the principle that the presence of a predetermined gas within an optical resonator will change the rate of decay of a coherent signal resonating within the optical resonator. The change in the rate of decay may occur either because the gas changes the frequency of resonance or level of absorption of an optical signal resonating within the resonator.

Cavity ring-down spectroscopy devices require precise timing between a coherent energy source that excites the resonator and the measurement of signal decay. In general, signal decay typically occurs within a few microseconds. Accordingly, the deactivation of the coherent source and subsequent signal measurements must be highly coordinated. However, there are a number of factors that can disrupt this process and the results. Accordingly, a need exists for better methods of controlling this process.

DETAILED DESCRIPTION OF AN ILLUSTRATED EMBODIMENT

Figure 1:
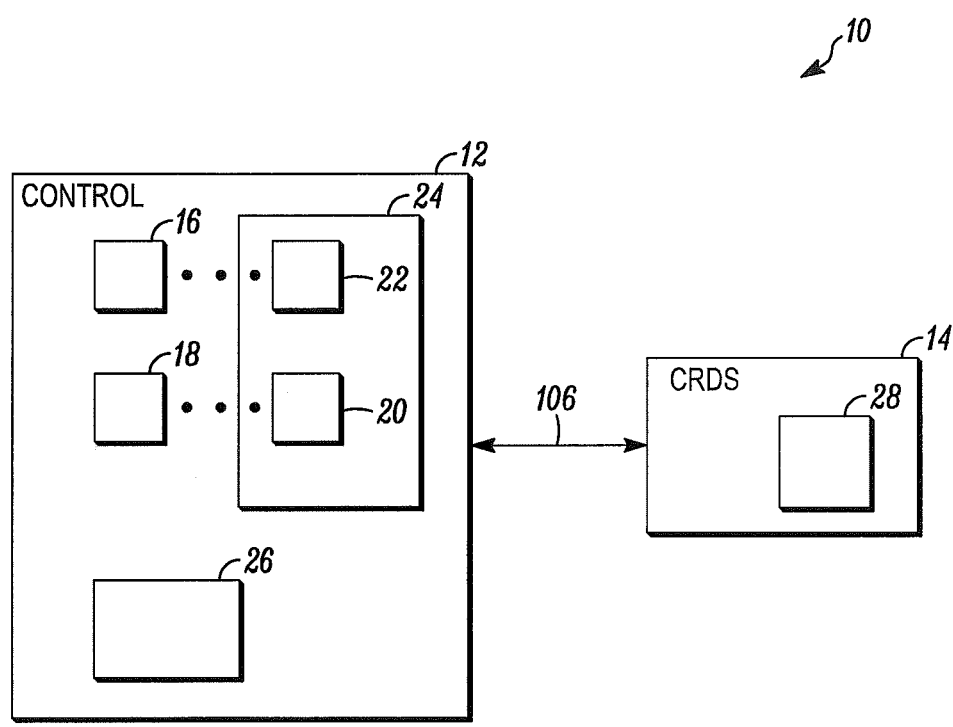
FIG. 1 is a block diagram of a cavity ring-down spectroscopy measurement system, shown generally in accordance with an illustrated embodiment.

FIG. 1 is a block diagram of a cavity ring-down spectroscopy measurement system 10 shown generally in accordance with an illustrated embodiment of the invention. Shown in FIG. 1 are a controller 12 and a cavity ring-down resonator assembly 14.

The system 10 addresses a problem that has not been previously recognized in the art of cavity ring-down spectroscopy. The problem not recognized is that of accurately and dispositively extinguishing (or otherwise cutting off) the delivery of coherent energy from a coherent energy source into a ring-down spectroscopy resonator at the beginning of the ring-down measurement process.

For example, when practiced with a continuous wave (cw) laser, the accurate use of cavity ring-down spectroscopy (CRDS) requires a means to extinguish the incident laser beam emanating from the CW laser very quickly after deactivation (e.g., less than 100 nanoseconds) with a high extinction ratio. If the extinction ratio is not sufficient, then light leaking into the CRDS resonator cavity for a short period after deactivation of the laser (i.e., during the "off" state) continues to pump the cavity and causes the ring-down signal to deviate from a purely decaying exponential. The error caused from this deviation results in a biased estimate of the true absorption coefficient. It has been further found that the bias is dependent upon the concentration of the gas being measured. Such a situation can be detrimental to the system performance in its effect on false alarms and detection of actual threshold events (the predicted concentration does not accurately represent the actual concentration).

In general, the problem of extinguishing coherent energy from a laser source may originate from any number of sources. For example, lasers, inherently, have their own resonators albeit much smaller than the resonator cavity of the CRDS resonator. Alternatively, the signal that deactivates the laser may not have a quick transition from the "on" state to the "off" state. In either situation, the result is that coherent energy emanating from a laser source may have its own decay rate.

Under illustrated embodiments, a switch system may be used to rapidly extinguish the coherent energy from the coherent source. To illustrate these concepts, tests were conducted using ammonia ($NH_3$) as a test gas within a CRDS resonator tuned to approximately 1510 nm. In this case the CRDS resonator had a cavity decay time (ring down time) of approximately 5 microseconds. An acoustic optic modulator (AOM) was used as an optical switch to directly modulate the extinction ratio or rate of decay of the coherent energy emanating from the laser source and entering the CRDS resonator.

Table I illustrates the results of these tests. Table I illustrates the error resulting from a very difficult testing environment using a 150 part per billion (ppb) $NH_3$ test gas introduced into a CRDS resonator and with varying laser extinction rates controlled by the AOM. The AOM Leakage in db shown in Table I were all measured at 50 nanoseconds (ns). As can be seen from Table I, for a −90 dB extinction rate at 50 ns, the CRDS resonator accurately measured the test gas at 150 ppb. As may also be observed from Table I, a −20 dB extinction rate at 50 ns resulted in a ½% error and a −15 dB extinction rate resulted in a 1.4% error. Further testing found that an optimum accuracy occurred at a −60 dB extinction rate at 50 ns.

TABLE I

| AOM Leakage (dB) | Predicted $NH_3$ Concentration (ppb) |
| --- | --- |
| −90 | 150 |
| −20 | 149.3 |
| −15 | 147.9 |
| −12.5 | 146.3 |
| −10 | 143.6 |
| −7 | 137.6 |
| −6 | 105.4 |

These tests were then generalized by comparing the extinction rate of the optical source with the ring-down rate of the CRDS resonator. Here it was found that optimum results occurred where an extinction rate of optical resonance within the CRDS resonator is at least 100 times longer than an extinction rate of optical energy emitted from the laser source.

Figure 2:
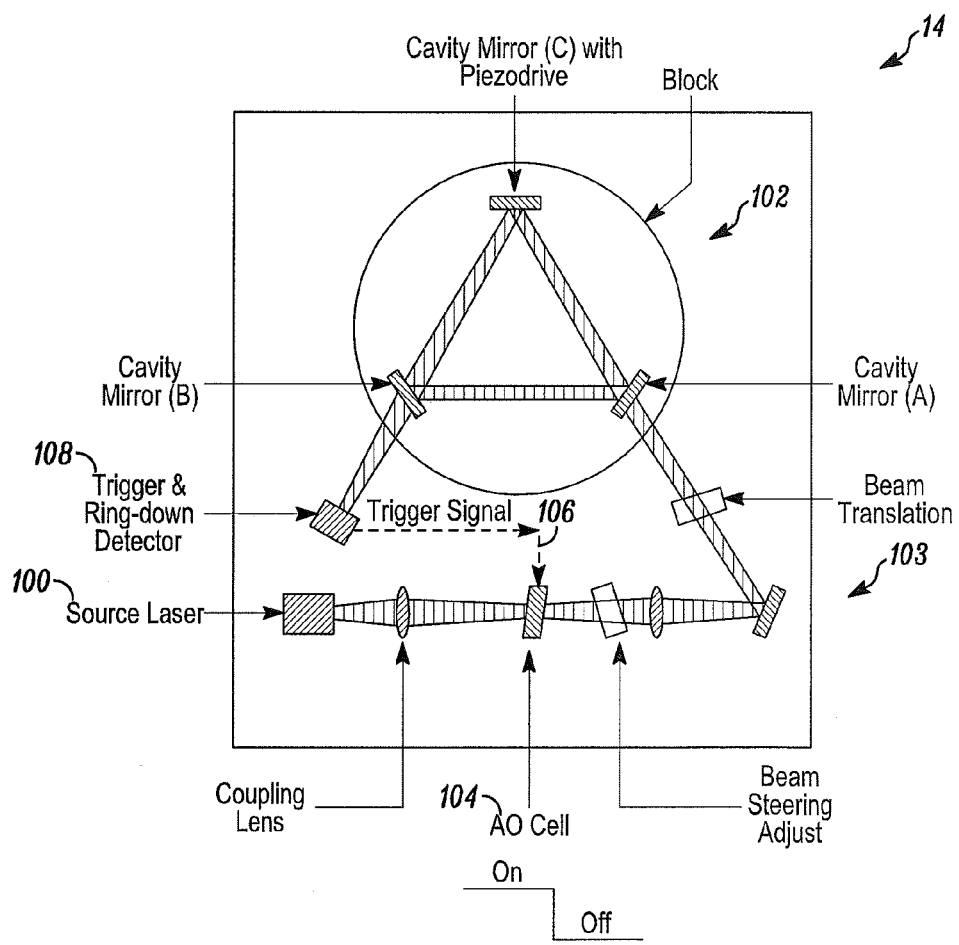
FIG. 2 is a block diagram of a specific type of cavity ring-down spectroscopy device that may be used with the system of FIG. 1.
Figure 3:
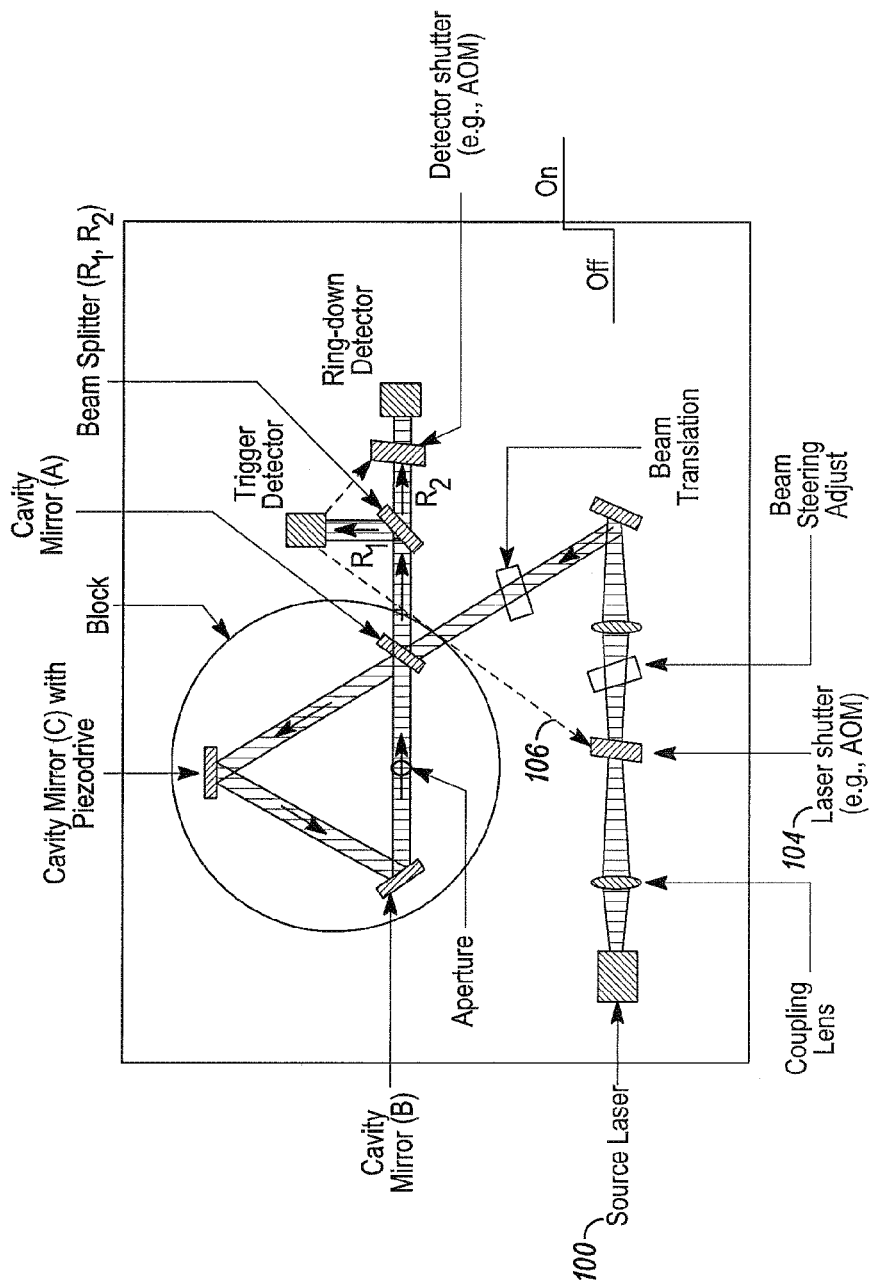
FIG. 3 is a block diagram of another specific type of cavity ring-down spectroscopy device that may be used with the system of FIG. 1.

FIGS. 2 and 3 are two examples of cavity ring-down resonators 14 that may be used within the system 10 of FIG. 1. FIGS. 2 and 3 both include a resonator cavity assembly 102 for measuring the concentration of a gas and a coherent exciter 103. As noted above, the laser sources 103 were adapted to have an extinction rate that is at least 100 faster than the ring-down rate of the resonator cavities 102.

FIG. 2 differs from FIG. 3 in the way in which coherent energy is introduced into and received from the resonator cavities 102. In this regard, FIG. 2 shows a resonator assembly that uses a first splitter combiner (Cavity Mirror A) to introduce coherent energy from the exciter 103 into the cavity assembly 103 and a second splitter combiner (Cavity Mirror B) to route coherent energy out of the cavity assembly 102 into the detector 108.

In contrast, the resonator cavity of FIG. 3 uses a single splitter combiner (Cavity Mirror A) to both introduce coherent light into the cavity 102 and receive light from the cavity 102. The resonator assembly 14 of FIG. 3 also relies upon the use of a second acoustic optic modulator positioned upstream of the detector.

The controller 12 of FIG. 1 includes one or more processors (implemented as hardware) 16, 18 programmed to operate under control of one or more computer programs 20, 22 embodied as respective sets of program steps loaded from a non-transitory computer readable medium (memory) 24. As used herein, reference to the functionality of a program 20, 22 is also a reference to the processor 16, 18 that executes that program to accomplish that functionality. A user interface 26 (including a display and keyboard) that allows a user to control the system 10 is also provided.

In this regard, the system 10 may include a respective set of programs 20, 22 for each target gas to be detected and measured by the system 10. In this regard, each respective set of programs 20, 22 for measuring a gas may include at least a sequence processor 16, 18 that uses a first time period for activation of the laser 100 and a second time period for measuring a ring-down time of the resonator cavity 102. The first time period may be initiated by a first instruction issued by the program 20, 22 that activates the laser 100. At the end of the first time period, the program 20, 22 issues an instruction 106 deactivating the laser 100 and activating a measurement program 20, 22 that collects readings from the detector 108. In this regard, a sample rate from the detector during the measurements may be specific to the target gas.

In general, the more rapid extinction rate of the laser source 103 may be achieved using any of a number of different methods. Under one illustrated embodiment, the laser source 103 may use a laser switch 28 (FIG. 1) to improve the extinction rate of the laser 100. The switch 28 may be embodied as an AOM laser shutter or switch 104 as shown in FIGS. 2 and 3. In this case the laser 100 and AOM switch 104 may operate under control of one or more control signals 106 from the sequence processor 16, 18.

The AOM switch 104 may be implemented as a single pass device or as a double pass device. For example, the AOM switch 104 may be implemented as the double pass switch assembly 400 shown in FIG. 4. In this case, the laser may be coupled through an optional variable optical attenuator (VOA) into a circulator T. The circulator has two outlets ports "1" and "R". In this situation, the control signal 106 would be directed to the AOM of FIG. 4.

Figure 4:
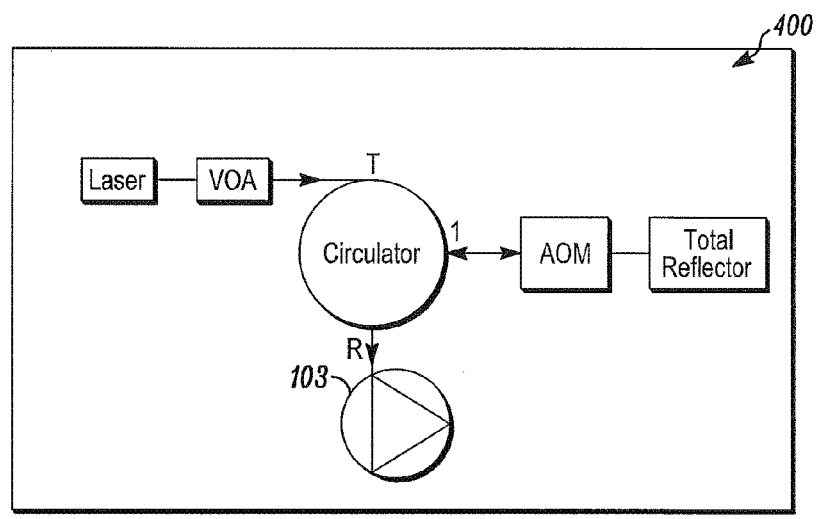
FIG. 4 is an optical switch that may be used with the system of FIG. 1.

In the activated state, the AOM of FIG. 4 would pass light to the total reflector that would, in turn, reflect coherent energy back into the circulator T and into the CRDS resonator 103 through the port "R". In a deactivated state, the AOM would extinguish coherent energy leaking into the cavity 103 from the instant of deactivation by at least −60 dB within 50 ns.

Figure 5:
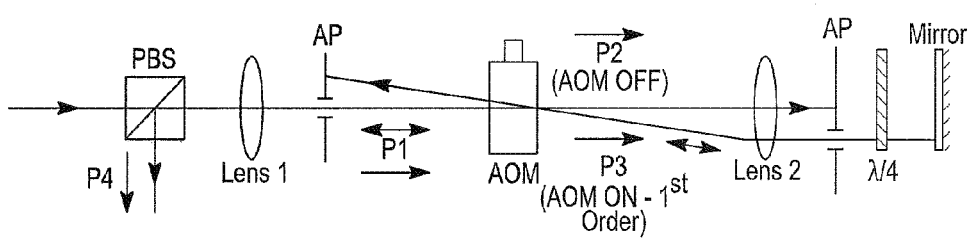
FIG. 5 is an alternative embodiment of a switch that may be used with the system of FIG. 1.

The AOM switch 104 may also be implemented as a double pass device such as that shown in FIG. 5. In this case, coherent energy from the laser 100 would enter from the left and impinge on the AOM device of FIG. 5 through the beamsplitter PBS. In the activated state, the AOM interacts with the optical energy and (via devices AP, lens, $\lambda/2$ device and mirror) reflects the coherent energy P4 into the resonator 103. Similarly, in the deactivated state, the AOM interacts with the optical energy and (via devices AP, lens, $\lambda/2$ device and mirror) extinguishes coherent energy from the instant of deactivation by at least −60 dB within 50 ns.

In still another embodiment, the laser switch 28 may be embodied as a high speed amplifier used in conjunction with a laser diode. In this case, the amplifier 28 may have a slew rate in the order of at least 100 volts per microsecond in order to deactivate the laser diode and extinguish an output from the laser diode by at least −60 dB within 50 ns.

In general, the system 10 may be embodied as a laser source and a ring-down optical resonator that performs cavity ring-down spectroscopy, the optical resonator receives coherent optical energy from the laser, wherein an extinction rate of optical resonance within the optical resonator (i.e., the cavity ring down time) is at least 100 times longer than an extinction rate of optical energy emitted from the laser source first following deactivation of the laser source.

In other embodiments, the system may include a resonator cavity, a laser coupled to the resonator cavity that excites the resonator cavity with coherent energy from the laser, a controller that sends an instruction that deactivates the laser, a controller that measures an exponential decay of energy within the resonator cavity from the instance of the instruction and a switch coupled to the controller that extinguishes coherent energy coupled from the laser to the resonator cavity at least 100 times faster than the ring down time of the resonator cavity after the instance of the instruction. The system may also include the context wherein the resonator cavity, the laser and the controller further comprise a cavity ring down spectroscopy detector. The system may also include the context wherein the switch extinguishes coherent energy coupled from the laser to the resonator within 50 nanoseconds of the instance of the instruction.

The system may also include the context wherein the switch further includes an acoustic optic modulator.

The system may also include a mirror that defines a portion of a path of coherent energy between the laser and resonator cavity where the mirror reflects the coherent energy received from the acoustic optic modulator back through the acoustic optic modulator. The system may also include the context wherein the switch further comprises a pair of acoustic optic modulators.

In other embodiments, the system may include a resonator cavity of a cavity ring down spectroscopy detector, a laser coupled to the resonator cavity, a controller that sends a first instruction to the laser, the laser responding by exciting the resonator cavity of the cavity ring down spectroscopy detector with coherent energy from the laser, a controller that sends a second instruction that deactivates the laser, a controller that measures an exponential decay of energy within the resonator cavity from the instance of the second instruction and a switch coupled to the controller that extinguishes coherent energy coupled from the laser to the resonator cavity within 50 nanoseconds of the instance of the second instruction.

The system may also include the context wherein the switch further comprises an acoustic optic modulator. The system may also include a mirror that defines a portion of a path of coherent energy between the laser and resonator cavity where the mirror reflects the coherent energy received from the acoustic optic modulator back through the acoustic optic modulator. The system may also include an optical splitter that receives coherent energy from the laser that transmits coherent energy to the resonator cavity, that transmits coherent energy to the acoustic optic modulator and that receives coherent energy from the acoustic optic modulator. The system may also include a pair of acoustic optic modulators.

Although a few embodiments have been described in detail above, other modifications are possible. For example, the logic flows depicted in the figures do not require the particular order shown, or sequential order, to achieve desirable results. Other steps may be provided, or steps may be eliminated, from the described flows, and other components may be added to, or removed from, the described systems. Other embodiments may be within the scope of the following claims.

The invention claimed is:

1. An apparatus comprising:
   a laser source;
   a ring-down optical resonator that performs cavity ring-down spectroscopy; and
   a controller that controls activation and deactivation of the laser source,
   wherein, when the controller activates the laser source, the optical resonator receives coherent optical energy from the laser source,
   wherein, when the controller deactivates the laser source, optical energy emitted from the laser source into the optical resonator is extinguished at least 100 times faster than a ring-down time of the optical resonator following an instance of deactivation of the laser source with an attenuation of the optical energy from the laser source of at least −50 dB,
   wherein the laser source includes an optical switch implemented as a double pass device, and
   wherein the controller includes a processor programmed to operate under control of executable software stored on a non-transitory computer readable medium.

2. The apparatus as in claim 1 wherein the optical switch further comprises an acoustic optical modulator.

3. The apparatus as in claim 1 further comprising a detector that samples an acoustic signal from the ring-down resonator.

4. The apparatus as in claim 3 wherein the laser source further comprises an amplifier driven by the controller.

5. An apparatus comprising:
   a resonator cavity;
   a laser coupled to the resonator cavity that excites the resonator cavity with coherent energy from the laser;
   a controller that sends an instruction that deactivates the laser;
   a detector that measures an exponential decay of energy within the resonator cavity from an instance of the instruction; and
   a switch coupled to the controller,
   wherein the controller controls the laser and the switch to extinguish the coherent energy coupled from the laser to the resonator cavity at least 100 times faster than a ring down time of the resonator cavity after the instance of the instruction with an attenuation of the laser's optical energy of at least −50 dB,
   wherein the switch is implemented as a double pass device, and
   wherein the controller includes a processor programmed to operate under control of executable software stored on a non-transitory computer readable medium.

6. The apparatus as in claim 5 wherein the switch further comprises an acoustic optic modulator.

7. The apparatus as in claim 5 wherein the switch further comprises a pair of acoustic optic modulators.

8. An apparatus comprising:
   a resonator cavity of a cavity ring down spectroscopy detector;
   a laser coupled to the resonator cavity;
   a controller that sends first and second instructions to the laser, the laser responding to the first instruction by exciting the resonator cavity of the cavity ring down spectroscopy detector with coherent energy from the laser, and the laser responding to the second instruction by deactivating the laser;
   a detector that measures an exponential decay of energy within the resonator cavity from an instance of the second instruction; and
   a switch coupled to the controller,
   wherein the controller controls the laser and the switch to extinguish the coherent energy coupled from the laser to the resonator cavity at least 100 times faster than a ring down time of the resonator cavity after the instance of the second instruction with an attenuation of the laser's optical energy of at least −50 dB,
   wherein the switch is implemented as a double pass device, and
   wherein the controller includes a processor programmed to operate under control of executable software stored on a non-transitory computer readable medium.

9. The apparatus as in claim 8 wherein the switch further comprises an acoustic optic modulator.

10. The apparatus as in claim 8 wherein the switch further comprises a pair of acoustic optic modulators.

* * * * *